(12) United States Patent
Stanslas et al.

(10) Patent No.: US 10,780,138 B2
(45) Date of Patent: Sep. 22, 2020

(54) EXTRACT OF ANDROGRAPHIS PANICULATA FOR COGNITIVE ENHANCEMENT

(71) Applicant: Universiti Putra Malaysia (UPM), Serdang, Selangor (MY)

(72) Inventors: Johnson Stanslas, Selangor (MY); Dahiru Sani, Selangor (MY); Hamidon Basri, Selangor (MY); Md. Shariful Hasan Sumon, Selangor (MY); Chee Woei Lim, Selangor (MY); Charng Choon Wong, Selangor (MY); Mohd Al-Saufreen Akhiruddin, Selangor (MY); Audrey Chee Hui Yong, Selangor (MY); Brian Patrick Kirby, Dublin (IE)

( * ) Notice: Subject to any disclaimer, the term of this patent is extended or adjusted under 35 U.S.C. 154(b) by 0 days.

(21) Appl. No.: 16/094,405

(22) PCT Filed: Jul. 18, 2017

(86) PCT No.: PCT/MY2017/000025
§ 371 (c)(1),
(2) Date: Oct. 17, 2018

(87) PCT Pub. No.: WO2017/204619
PCT Pub. Date: Nov. 30, 2017

(65) Prior Publication Data
US 2019/0125814 A1 May 2, 2019

(30) Foreign Application Priority Data
May 23, 2016 (MY) .......................... PI 2016701854

(51) Int. Cl.
| | | |
|---|---|---|
| *A61K 36/19* | (2006.01) | |
| *A61K 31/365* | (2006.01) | |
| *A61K 31/7048* | (2006.01) | |
| *A23L 33/105* | (2016.01) | |
| *A61K 38/16* | (2006.01) | |
| *A61P 25/00* | (2006.01) | |
| *A61K 9/00* | (2006.01) | |

(52) U.S. Cl.
CPC ............ *A61K 36/19* (2013.01); *A23L 33/105* (2016.08); *A61K 9/0053* (2013.01); *A61K 31/365* (2013.01); *A61K 31/7048* (2013.01); *A61K 38/168* (2013.01); *A61P 25/00* (2018.01); *A23V 2002/00* (2013.01); *A61K 2236/00* (2013.01); *A61K 2236/17* (2013.01); *A61K 2236/331* (2013.01)

(58) Field of Classification Search
None
See application file for complete search history.

(56) References Cited

U.S. PATENT DOCUMENTS 8,859,012 B2 * 10/2014 Chan ..................... A23L 33/11
424/725

FOREIGN PATENT DOCUMENTS

| WO | 2005104722 A2 | 11/2005 |
| WO | 2011086007 A1 | 7/2011 |
| WO | 2014176149 A1 | 10/2014 |

OTHER PUBLICATIONS

Hui, Y.W., et al., "Modulation of Cell Surface Hydrophobicity and Attachment of Bacteria to Abiotic Surfaces and Shrimp by Malaysian Herb Extracts." Journal of Food Protection, 2012, 75(8): 1507-1511.

Kumar, S., et al., "Extraction of Three Bioactive Diterpenoids from Andrographis paniculata: Effect of the Extraction Techniques on Extract Composition and Quantification of Three Andrographolides Using High-Performance Liquid Chromatography." Journal of Chromatographic Science, 2014, 52: 1043-1050.

Thakur, A.K., et al., "Beneficial effects of an Andrographis paniculata extract and andrographolide on cognitive functions in streptozocin-induced diabetic rats." Pharmaceutical Biology, 2016, 54(9): 1528-1538.

* cited by examiner

*Primary Examiner* — Susan Hoffman
(74) *Attorney, Agent, or Firm* — Saliwanchik, Lloyd & Eisenschenk

(57) ABSTRACT

The present invention provides an aqueous extract of *Andrographis paniculata* leaves containing as main components andrographolide, neoandrographolide and 14-deoxy-11,12-didehydroandrographolide. The Invention also provides a method of production of said extract, comprising the steps of drying the leaves of *Andrographis paniculata*, and extracting them with water at a temperature of at least 50° C. The aqueous extract of *Andrographis paniculata* Leaves Is suitable for use as cognition enhancing agent having antineuroinflammatory and antioxidative effects.

3 Claims, 3 Drawing Sheets

EXTRACT OF ANDROGRAPHIS PANICULATA FOR COGNITIVE ENHANCEMENT

CROSS REFERENCE TO A RELATED APPLICATION

This application is a National Stage Application of International Application Number PCT/MY2017/000025, filed Jul. 18, 2017; which claims priority to Malaysian Application No. PI 2016701854, filed May 23, 2016.

FIELD OF ART

The present invention relates to the extract of *Andrographis paniculata*, method of preparation and use thereof.

BACKGROUND ART

The rapid growth of aged population in developed countries, including Malaysia, is increasing. Higher age is rather often connected with cognitive impairment, such as memory loss, dementia. Alzheimer disease etc. To date, there is no cure to treat or prevent cognitive impairment. Herbal supplements are the only source of any memory improvement. Through research over many years, medical scientists have come to the conclusion that chronic neuroinflammation, oxidative damage and altered neurotransmitter actions are the main causative factors for disrupting neuroplasticity. At present, the most active commercially available herbal-based cognition enhancer is *Ginkgo biloba* extract.

There is thus an urgent need to search for new cognition enhancing agents, which would be more active and which would make a valid alternative to the existing treatments. It would also be preferable if the new agent was less expensive than the existing treatments.

*Andrographis paniculata* (hempedu bumi) is a herb found throughout Asia. It is reported to have many medicinal properties and has been used to treat upper respiratory disorders, several infectious diseases, diabetes and hypertension. Recent reports highlighted the protective role of andrographolide, the main bioactive component of *Andrographis paniculata*, in oxidative stress in the brain caused by nicotine-induced toxicity in combination with vitamin E (Das et al, Appl. Phy Nut Met 2009, 34: 124-135), cerebral ischaemia in rats (Chan et al. Br J Pharmacol 2010, 161(3); 668-679) and hypoxia-induced oxidative/nitrosative brain injury provoked by cerebral ischemic/reperfusion injury in mice (Chang et al., Toxicol App Pharmacol 2011, 257(1): 137-147).

Plant extracts so far have been prepared mostly using organic solvents, such as alcohols, ethers, alkanes, chlorinated solvents. However, any use of organic solvent results in traces of the solvent in the product, said traces of the solvents being potentially harmful for the patient.

DISCLOSURE OF THE INVENTION

The present invention provides an aqueous extract of *Andrographis paniculata* leaves containing as main components andrographolide (AGP) in an amount of 1-4 wt. %, neoandrographolide (NAG) in an amount of 1-3 wt. % and 14-deoxy-11,12-didehydroandrographolide (DDAG) in an amount of 0.05-0.2 wt. %. The extract contains 0.2-0.7 wt. % proteins, 0.01-0.05 wt. % polysaccharides, and 15-25 wt. % glycosaponins.

The extract can be produced by drying the leaves of *Andrographis paniculata* and extracting them with water at a temperature of at least 50° C., preferably 55 to 70° C. Preferably, the extraction is made without the addition of any other solvent. This avoids the need for removing the remaining non-aqueous solvent which might be potentially harmful for the organism treated by the extract. Drying the leaves is preferably performed in an oven dryer at the temperature of at least 30° C., preferably of 40 to 70° C. with subsequent powdering. The extract is preferably used in a solid form, obtained from the liquid extract by freeze-drying.

The aqueous extract of *Andrographis paniculata* leaves is suitable for use as cognition enhancing agent having anti-neuroinflammatory and antioxidative effects. It may be used for the treatment, amelioration or prevention of cognitive impairment, such as memory loss, stress, dementia or Alzheimer disease.

The inventors of the present invention have found that the extract of *Andrographis paniculata* leaves has therapeutic effect in animal model of LPS induced neuroinflammation, and has anti-neuroinflammatory, antioxidant and anticholinergic activities that promote neuroprotection and enhances memory in neuro-inflammatory induced animals. Furthermore, the Morris Water Maze test shows that the extract enhances cognitive functions. All these results of various tests show that the extract of the present invention is useful as a cognition enhancer in subjects in need of such treatment.

The present invention provides also a composition for treatment, amelioration or prevention of cognitive impairement, in particular a food supplement, containing the extract and at least one auxiliary substance acting as carrier, such as a filler, a binder, or a solvent. Pharmaceutically acceptable fillers, binders and solvents are well known to those skilled in the field. The composition is preferably in the form of an oral formulation, preferably a tablet or capsule.

EXAMPLES OF CARRYING OUT THE INVENTION

Example 1

Preparation of the Extract

Figure 1:
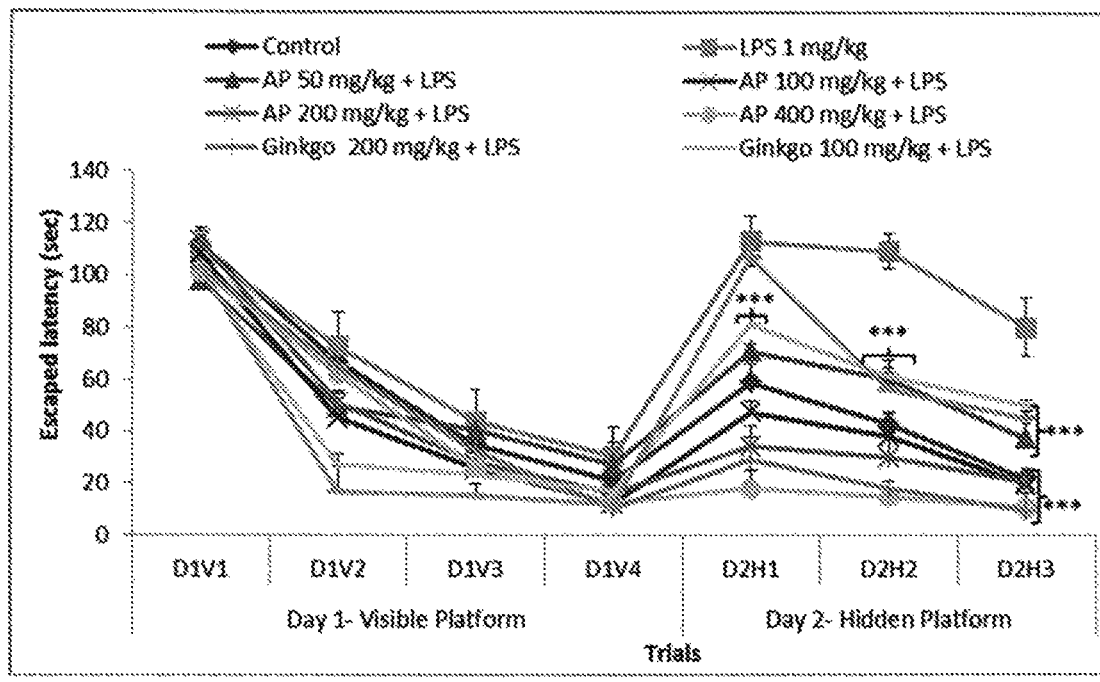
FIGS. 1 and 2 shows the results of evaluation of the effect of AP extract on the prevention of cognitive impairment in rats using Morris Water Maze task.

Leaves of *Andrographis paniculata* were harvested and washed thoroughly with running tap water, thereafter subjected to three successive changes in ultrapure distilled water and dried at 40° C. in an oven dryer for 3 days before being powdered using a blender MX-800S (Panasonic). Extraction of the powdered leaves sample was done with water at ratio of 1:20 (w/v).

The mixture was mixed thoroughly, heated at 60° C. for 5 hours with frequent stirring and then filtered through Whatman No. 1 filter paper. Thereafter, the filtrate (extract) was freezed to −80° C. overnight and dried to powder form in a freeze dryer. The yield was approximately 12.3% (w/w) of dried leaves. The standardized *Andrographis paniculata* extracts is used in in vivo tests for cognitive assays.

Quantities of primary and secondary metabolites of *Andrographis paniculata* in this extract are shown in Tables 1 and 2. Quantities of primary metabolites were determined according to Malaysian Standard (2013), quantities of secondary metabolites were determined using HPLC.

TABLE 1

Primary metabolites

| Parameter | |
|---|---|
| Protein (%) | 0.50 ± 0.00 |
| Polysaccharide (%) | 0.03 ± 0.00 |
| Glycosaponin (%) | 20.20 ± 0.2 |

TABLE 2

Secondary metabolites

| | Andrographolide | Neoandrographolide | 14-deoxy-11,12-didehydro-andrographolide |
|---|---|---|---|
| Amount in extract | 2.96 ± 0.36 | 1.81 ± 0.22 | 0.11 ± 0.02 |

Example 2

Effect of Standardised Aqueous Extract of AP on LPS Induced Cognition Impairement Morris water maze (MWM) test is a well-established behavioural task for studying spatial learning and memory in animal model (Morris 1984). Rats were tested for cognitive function using a 2-day protocol as described by Gulinello et al. (2009) with a slight modification. Briefly, following seven days pre-treatment with AP, EGb or vehicle, the animals were trained in a pool of water tank with dark background containing a visible platform with different contrast to the inner black surface of the tank which is about 2 cm above the water surface. The training consists of four trials on the first day, and is designated V1-V4 (visible platform trial 1-4) or D1V1-4 (day 1, visible platform trial 1-4). During the training trials, the animals are expected to learn to find the platform within 120 sec and escape. Animals that failed to escape within the 120 sec were guided manually to the platform. All animals stayed on the platform for 15 sec before being removed, dried and then placed in a separate dry cage. Thereafter, the experimental animals were injected with LPS. After 24 h, the animals were tested in a series of three hidden platform trials (T1-T3) then followed by a probe trial, consisting of a single 30 sec trial performed 24 h later in a pool without platform. Data including swim latency, path length, swimming speed during all the trials were recorded using ANY-maze Video Tracking System (Stoelting, Wood Dale, Ill. USA), connected to a webcam. All data were thereafter used to assess performance as well as motor activity in the water maze task. Similarly, latency to enter and the time spent in the novel quadrant during the probe trial was also captured and analysed.

Example 3

Determination of Level of Pro-Inflammatory Cytokine

Brain cytosolic supernatant was analysed for the presence of immunoreactive IL-1β, TNF-α and IL-6 levels using commercial ELISA kit according to protocols provided by the manufacturer (Cusabio Biotech Co. Ltd, Wuhan, China) and the results were expressed as pg/mL.

Example 4

Measurement of Oxidative Stress Markers

The generation of intracellular ROS in the brain section lysates was measured using 2, 7-dichlorofluorescin diacetate (DCF-DA) as earlier described by Shinomol & Muralidhara (2011). Briefly, reaction mixture (1 mL Lockes buffer pH 7.4, 0.2 mL cytosol fraction and 10 µl of 5M DCFH-DA) was incubated at room temperature for 15 min. Following 30 min of further incubation, the formation of the fluorescent product DCF was measured using spectrofluorimeter (484-nm excitation and 530-nm emission). ROS generation was reported as fold change against control.

Lipid peroxidation level was estimated based on the MDA index using the thiobarbiturate acid reactive substance (TBARS) assay as described by Draper & Hadley (1990) with a slight modification and expressed as fold change against control. The TBARS test is usually used to measure the pink MDA—TEA product formed under high temperature (90-100° C.) and acidic condition reaction (Gupta et al. 2003). Briefly, 200 µl of 20% trichloroacetic acid (TCA) was added to 50 µl of the brain section homogenate, mixed and then centrifuged at 4,000 rpm for 20 min. Equal volume of the supernatant was then mixed with thiobarbituric acid (TBA) reagent. Similar treatment was also carried out for the reagent blank. The content of each sample was then heated on water bath at 95° C. for 10 min, cooled and the absorbance was measured at 532 nm in a UV-Visible double beam spectrophotometer (VersaMax microplate reader. Molecular devices, US).

Example 5

Measurement of Levels of Cholinesterase Enzyme Activities

Acetylcholinesterase (AChE) inhibition activity was determined by modifying the original method developed by Ellman et al. (1961). Using, a 96 well plate, 5 µl of sample (brain section homogenate) or blank (control) was added into each experimental well containing the reaction mixture (285 µl phosphate buffer (0.1 M, pH 8.0) and 5 µl (10 mM) DTNB). Then, 2 µl (150 mM) of acetylthiocholine iodide (used as substrate) was added and the change in the absorbance was monitored at 412 nm for 5 min using a spectrophotometer.

Principle: the hydrolysis of acetylthiocholine was shown by the formation of yellow 2-nitro-5-sulfidobenzene-carboxylate anion as the result of the reaction of DTNB with thiocholine, released by the enzymatic hydrolysis of acetylthiocholine.

Butyrylthiocholine iodide was used as a substrate to assay butyrylcholinesterase enzyme, while all the other reagents and conditions were the same as for acetylcholinesterase enzyme assay above.

Example 6

Measurement of Levels of Antioxidant Activities and Glutathione

The superoxide dismutase (SOD) and catalase (CAT) assays were performed using ELISA kit (Cayman Chemical Company, Ann Arbor, Mich. USA) in accordance with manufacturer's instructions. The optical density was read at 440 and 540 nm for SOD and CAT respectively using VersaMax microplate reader (Molecular devices, US).

Total reduced glutathione (GSH) was estimated by the method earlier adopted by Rajasekaran et al. (2004) with a slight modification. Briefly, aliquots of brain section homogenates from control or experimental, animals was precipitated by adding 5% TCA in 1:1 ratio and then centrifuged. An equal volume of the supernatant (10 µl) and 0.2M phosphate buffer (250 µl) was then mixed, followed by addition of 40 µl of DNTB reagent (0.6 mM) and the colour developed was read at 412 nm against control. The results were expressed as unit/mg of brain section (Mori et al. 2004).

The results of the tests are shown in the appended Figures.

The water maze test is a relative measure of cognitive abilities of the animal to learn and then remember the platform location (Guiinello et al. 2009). All the tested rats generally showed a decrease latency to locate the platform in the visible platform trial (day 1). The initial visible platform test is in accordance with previous studies (Schulz et al. 2007; Clinton et al. 2007; Galea et al. 2002) which reported assessment of baseline locomotor function, habituation rate as well as individual and treatment group differences in swimming speed as part of numerous advantages regarding the escape latency prior to the hidden platform trials (after 24 h delay) to evaluate long term spatial memory. Exposure of rats to LPS induces alteration in spatial learning and memory as assessed by the MWM test (FIG. 1).

Figure 2:
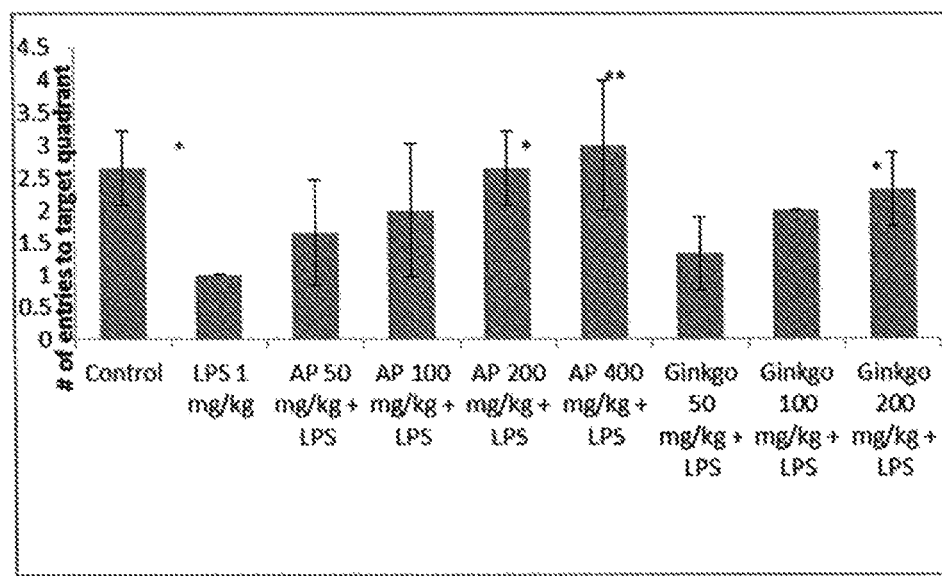

The ability of the rats to locate the target quadrant as well as total time spent in the target quadrant, during the probe test decreased significantly with LPS—induced neuro-inflammation. However, rats pre-treated with graded concentrations of AP showed a significant decreased latency to escape compared to the LPS control rats (P≤0.001). The result significantly (P≤0.001) revealed a clear evidence of learning with greater latency difference in the LPS control group compared to treated groups. Large number represents poorer performance while smaller number indicate they have learnt (in the visible platform, day 1) and can remember the location of the hidden platform in day 2 (Guiinello et al. 2009) (FIG. 2). Overall, AP was superior to Ginkgo biloba (EGb 761), particularly at lower doses (50 and 100 mg/kg), in improving the memory of animals (FIG. 1). Similarly, assessment of short term memory (difference in latency within trial of same day. (D2H2–D2H1) was also evaluated.

Figure 3:
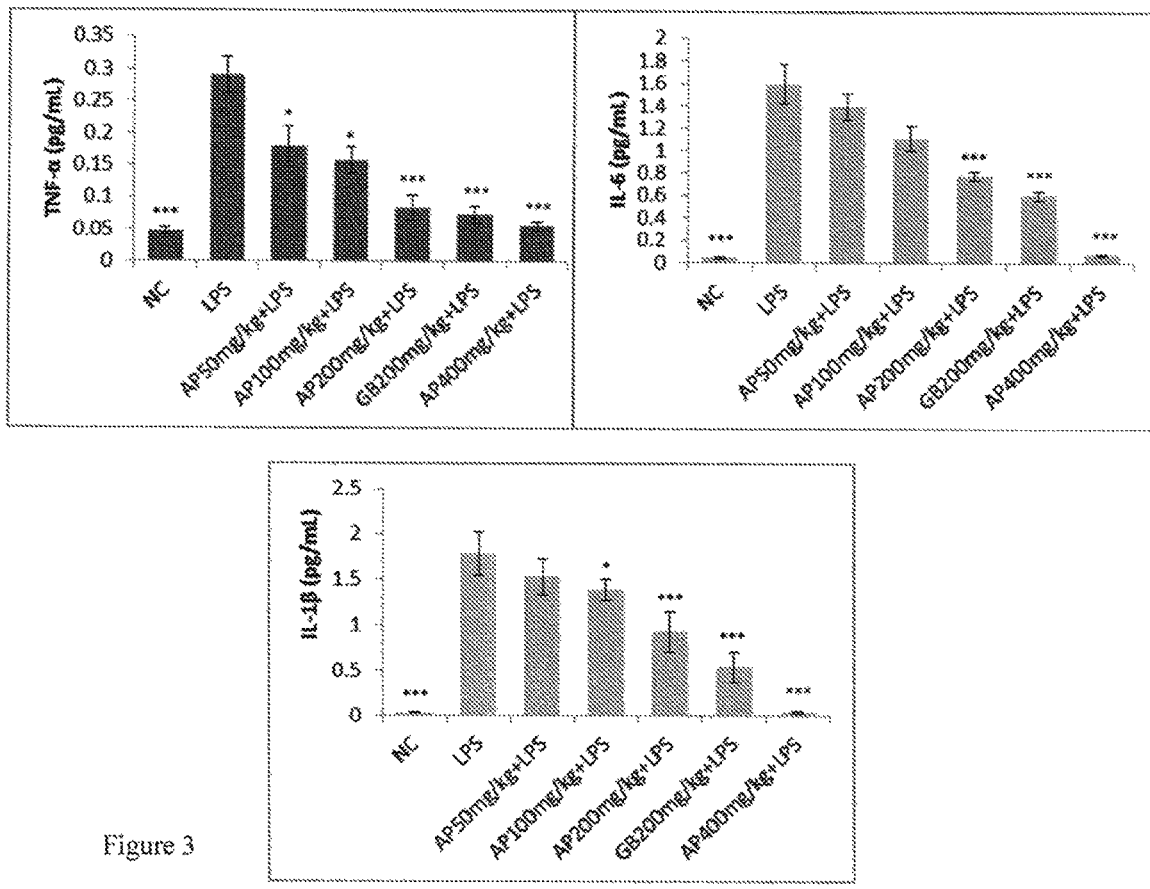
FIG. 3 shows the effect of standardised aqueous extract of AP or ginkgo on LPS induced production of pro-inflammatory cytokines (TNF-α, IL-6 and IL-1β). Values are expressed mean±SD (n=10). *P≤0.05, ***P≤0.001 compared to LPS group.

Substantial studies have also reported deficits in learning and memory as a result of neuro inflammation affecting hippocampal function (Gong et al. 2010; Lee et al, 2008;

Tanaka et al. 2006). We determined the levels of various pro-inflammatory cytokines (IL-1β, TNF-α, IL-6) in the hippocampus, a brain area where neuro-inflammation primarily takes place in response to brain injury and inflammation (McGeer & McGeer 2004; Ren et al. 1999). Compared with the LPS control, pre-treatment with graded doses of AP significantly suppressed the production of all the measured cytokines in a dose-dependent manner (FIG. 3).

Figure 4:
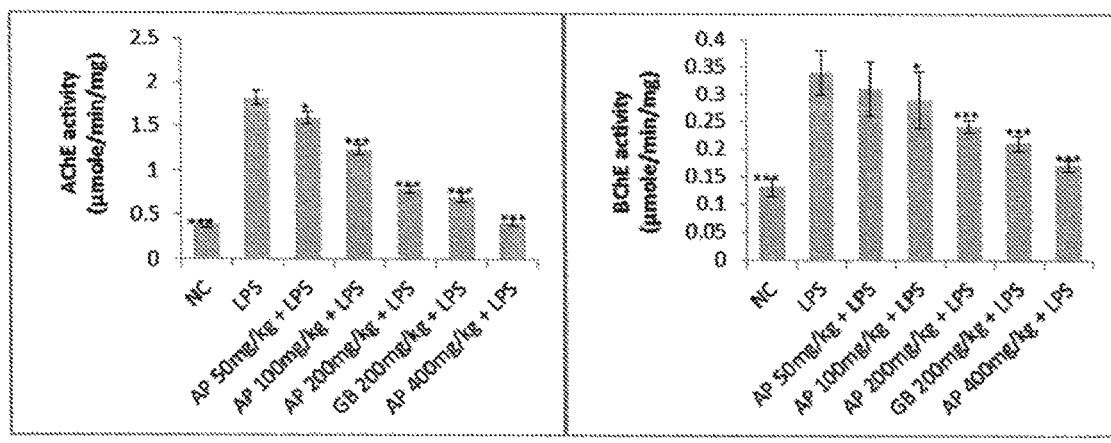
FIG. 4 shows the effect of standardised aqueous extract of AP or Ginkgo (GB) on LPS induced production of (A) ROS and (B) TBARS levels.

Increased levels of MDA has been reported to signify increased concentrations of free radicals (Sugino et al. 1987). In this study, immunoassay analysis showed increased concentration of cytokines and oxidative markers (ROS and TBARS) in the LPS-treated animals (FIG. 4), which could explain the compromised state of learning and memory due to impaired hippocampus functioning.

Figure 5:
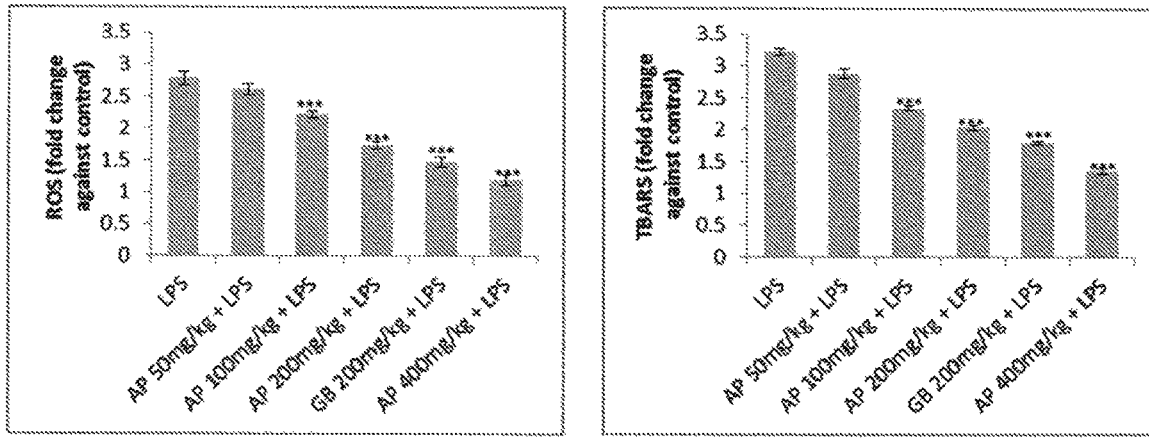
FIG. 5 shows the effect of pre-treatment of standardised aqueous extract of AP or Ginkgo (GB) against LPS induced up regulation of oxidative stress markers (ROS and TBARS).

More also, we measured the level of AChE activity in the hippocampus region of the brain as a marker of cholinergic activity. Administration of LPS significantly increased the activity of AChE in the brain of rats in the LPS control group which could signify decrease in cholinergic activities (FIG. 5). This means following administration of AP extract there will be an increase in acetylcholine level in the brain, an important neurotransmitter for cognition.

Figure 6:
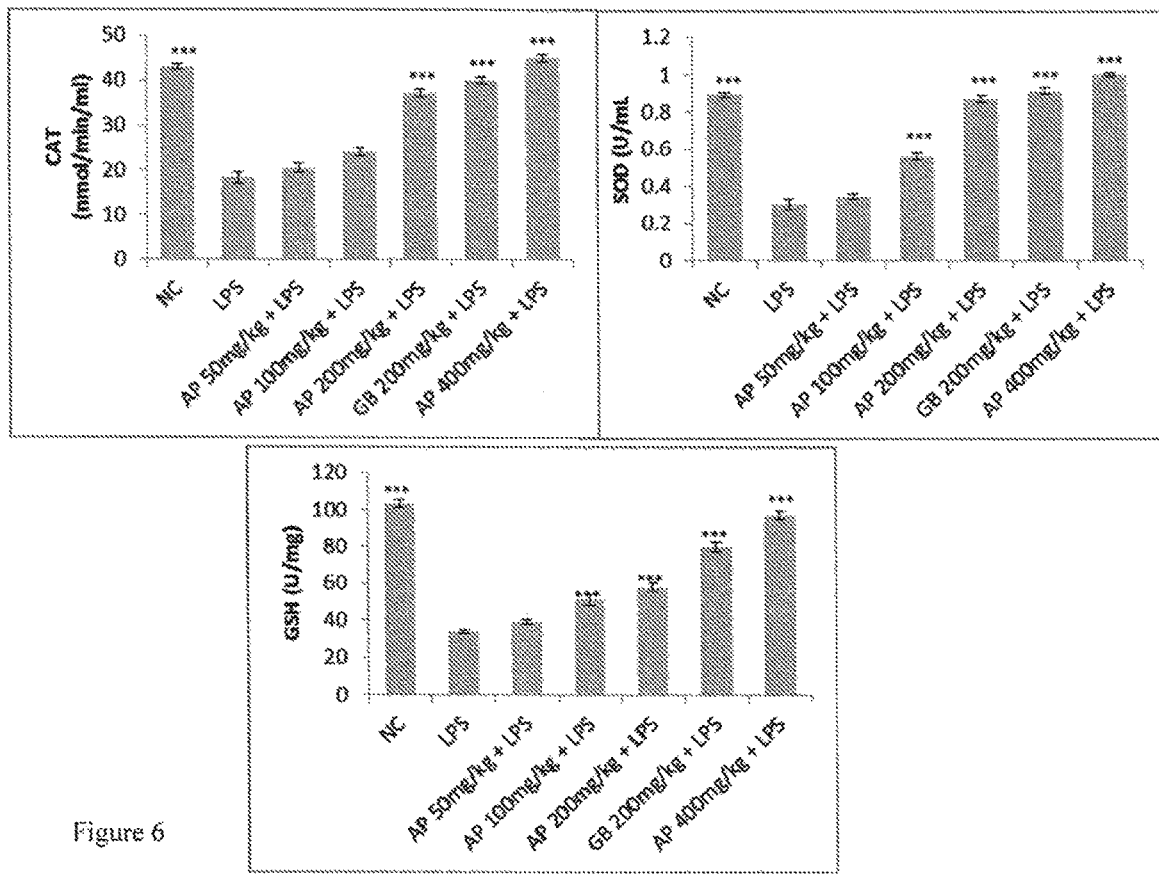
FIG. 6 shows the effect of pre-treatment of standardised aqueous extract of AP or Ginkgo (GB) on LPS induced decreased (A) SOD, (B) CAT activities and (C) GSH level.

Furthermore, LPS injection produces a significant reduction of antioxidant enzymes such as superoxide dismutase and catalase. However, treatment of rats with different doses of standardised aqueous AP extract significantly (P<0.05) ameliorated in a dose dependent manner the alterations induced with LPS (FIG. 6).

All above findings deduced that standardised aqueous AP extract protects the brain against LPS-induced neuro inflammation and enhances memory.

REFERENCES

1. Clinton. L. K. et al, 2007. Age-dependent sexual dimorphism in cognition and stress response in the 3×Tg-AD mice. *Neurobiology of disease,* 28(1), pp. 76-82.

2. Draper, H. H. & Hadley, M., 1990. *Oxygen Radicate in Biological Systems Part B: Oxygen Radicals and Antioxidants*, Elsevier.

3. Galea, L. A., et al, 2002. High levels of estradiol impair spatial performance in the Morris water maze and increase "depressive-like" behaviors in the female meadow vole. *Physiology & Behavior,* 77(2-3), pp. 217-225.

4. Gong, Q.-H. et al., 2010. Hydrogen sulfide attenuates lipopolysaccharide-induced cognitive impairment: a pro-inflammatory pathway in rats. *Pharmacology biochemistry, and behavior,* 96(1), pp. 52-8.

5. Gulinello, M. et al., 2009, Validation of a 2-day water maze protocol in mice. *Behavioural brain research,* 196(2), pp. 220-7.

6. Gupta, Y., Veerendra Kumar, M. & Srivastava, A., 2003, Effect of *Centella asiatica* on pentylenetetrazole-induced kindling, cognition and oxidative stress in rats. *Pharmacology Biochemistry and Behavior.* 74(3), pp. 579-585.

7. Lee, J. W. et al., 2008, Neuro-inflammation induced by lipopolysaccharide causes cognitive impairment through enhancement of beta-amyloid generation. *Journal of neuroinflammation,* 5, p. 37.

8. McGeer, P. L., & McGeer, E. G., 2004. Inflammation and the degenerative diseases of aging. *Annals of the New York Academy of Sciences,* 1035, pp. 104-116.

9. Morris, R., 1984, Developments of a water-maze procedure for studying spatial learning in the rat. *Journal of Neuroscience Methods,* 11(1), pp. 47-60.

10. Rajasekaran, N. S, et al., 2004, The effect of finger millet feeding on the early responses during the process of wound healing in diabetic rats. *Biochimica et biophysica acta,* 1689(3), pp. 190-201.

11. Ren, L. et al, 1999. Differential expression of inflammatory mediators in rat microglia cultured from different brain regions. *Molecular Brain Research,* 65(2), pp. 198-205.

12. Schulz, D. et al. 2007. "Despair" induced by extinction trials in the water maze: relationship with measures of anxiety in aged and adult rats. *Neurobiology of learning and memory,* 87(3), pp. 309-23.

13. Shinomol, G. K, & Muralidhara, 2011, *Bacopa monnieri* modulates endogenous cytoplasmic and mitochondrial oxidative markers in prepubertal mice brain. *Phytomedicine,* 18(4), pp. 317-326.

14. Sugino, K. et al, 1987. The role of lipid peroxidation in endotoxin-induced hepatic damage and the protective effect of antioxidants. *Surgery,* 101(6), pp. 746-752.

REFERENCES

15. Clinton, L. K. et al., 2007. Age-dependent sexual dimorphism in cognition and stress response in the 3xTg-AD mice. *Neurobiology of disease,* 28(1). pp. 76-82.

16. Draper, H. H. & Hadley, M, 1990. *Oxygen Radicals in Biological Systems Part B: Oxygen Radicals and Antioxidants,* Elsevier.

17. Galea, L. A. et al., 2002. High levels of estradiol impair spatial performance in the Morris water maze and increase "depressive-like" behaviors in the female meadow vole. *Physiology & Behavior,* 77(2-3), pp. 217-225.

18. Gong, Q.-H. et al., 2010. Hydrogen sulfide attenuates lipopolysaccharide-induced cognitive impairment: a proinflammatory pathway in rats. *Pharmacology biochemistry, and behavior,* 96(1), pp. 52-8.

19. Gulinello, M. et al. 2009. Validation of a 2-day water maze protocol in mice. *Behavioural brain research,* 196(2), pp. 220-7.

20. Gupta, Y., Veerendra Kumar, M., & Srivastava, A., 2003. Effect of *Centella asiatica* on pentylenetetrazole-induced kindling, cognition and oxidative stress in rats. *Pharmacology Biochemistry and Behavior,* 74(3), pp. 579-585.

21. Lee, J. W. et al., 2008. Neuro-inflammation induced by lipopolysaccharide causes cognitive impairment through enhancement of beta-amyloid generation. *Journal of neuroinflammation,* 5, p. 37.

22. McGeer, P. L, & McGeer, E. G., 2004. Inflammation and the degenerative diseases of aging. *Annals of the New York Academy of Sciences,* 1035, pp. 104-116.

23. Morris, R., 1984. Developments of a water-maze procedure for studying spatial learning in the rat. *Journal of Neuroscience Methods,* 11(1), pp. 47-60.

24. Rajasekaran, N. S. et al., 2004. The effect of finger millet feeding on the early responses during the process of wound healing in diabetic rats. *Biochimica et biophysica acta,* 1689(3), pp. 190-201.

25. Ren, L., et al., 1999. Differential expression of inflammatory mediators in rat microglia cultured from different brain regions. *Molecular Brain Research,* 65(2), pp. 198-205.

26. Schulz, D. et al, 2007. "Despair" induced by extinction trials in the water maze: relationship with measures of anxiety in aged and adult rats. *Neurobiology of learning and memory,* 87(3), pp. 309-23.

27. Shinomol, G. K. & Muralklhara, 2011. *Bacopa monnieri* modulates endogenous cytoplasmic and mitochondrial oxidative markers in prepubertal mice brain. *Phytomedicine,* 18(4), pp. 317-326.

28. Sugino, K, et al., 1987. The role of lipid peroxidation in endotoxin-induced hepatic damage and the protective effect of antioxidants. *Surgery,* 101(6), pp. 746-752.

The invention claimed is:

1. A method for enhancing cognition, said method comprising administering to a subject an aqueous extract of *Andrographis paniculata* leaves comprising 1-4 wt. % andrographolide, 1-3 wt. % neoandrographolide, and 0.05-0.2 wt. % 14-deoxy-11,12-didehydroandrographolide, wherein the aqueous extract contains primary metabolites of *Andrographis paniculata:* 0.2-0.7 wt. % proteins, 0.01-0.05 wt. % polysaccharides, and 15-25 wt. % glycosaponins.

2. The method according to claim 1, wherein the method is used for treatment, amelioration or prevention of memory loss, stress, dementia or Alzheimer disease.

3. The method, according to claim 1, wherein the administration of the aqueous extract has antineuroinflammatory and antioxidant effects.

* * * * *